United States Patent [19]

Pogany et al.

[11] 4,386,103

[45] May 31, 1983

[54] DICHLOROAMINO ACID DERIVATIVES USEFUL AS POTENT GERMICIDAL AND FUNGICIDAL AGENTS

[75] Inventors: Stefano A. Pogany; Takeru Higuchi, both of Lawrence, Kans.

[73] Assignee: Merck & Co., Inc., Rahway, N.J.

[21] Appl. No.: 229,805

[22] Filed: Jan. 30, 1981

[51] Int. Cl.[3] .................. A61K 31/225; A61K 31/95; C07C 69/40; C07C 69/42; C07C 101/10

[52] U.S. Cl. ...................................... 424/313; 560/87; 424/305; 424/309; 424/311; 424/312; 424/317; 424/318; 424/319; 560/38; 560/39; 560/118; 560/121; 560/122; 560/123; 560/124; 560/125; 560/170; 560/172; 560/193; 560/194; 560/196; 562/444; 562/449; 562/500; 562/503; 562/504; 562/505; 562/506; 562/507; 562/574; 260/404; 560/84; 560/85

[58] Field of Search .................. 560/39, 38, 170, 196, 560/84, 85, 118, 121, 122, 123, 124, 125, 172, 193, 194, 87; 562/444, 451, 500, 504, 503, 505, 506, 507, 567, 449, 574; 424/309, 310, 305, 311, 312, 313, 319, 318; 260/404

[56] References Cited

U.S. PATENT DOCUMENTS 3,796,756 3/1974 Bakker .
3,966,796 6/1976 Kaminski et al. .
4,036,843 7/1977 Kaminski et al. .
4,045,578 8/1977 Kaminski et al. .
4,171,452 10/1979 Kaminski et al. .

FOREIGN PATENT DOCUMENTS 1452263 10/1976 United Kingdom .

OTHER PUBLICATIONS

J. Vit et al., Synthetic Communications, 6(1), 1–4, (1976).

A. Strecker, Ann. 123, 363, (1862), Cited in Merck Index, Organic Name Reactions as "Strecker Degradation".

*Primary Examiner*—Natalie Trousof
*Assistant Examiner*—Vera C. Clarke
*Attorney, Agent, or Firm*—Theresa Y. Cheng; Mario A. Monaco; Michael C. Sudol, Jr.

[57] ABSTRACT

Dichloroamino acid derivatives other than α-dichloroamino acids are prepared from chlorination of corresponding amino acids, and are found to be potent germicidal and fungicidal agents.

10 Claims, No Drawings

DICHLOROAMINO ACID DERIVATIVES USEFUL AS POTENT GERMICIDAL AND FUNGICIDAL AGENTS

BACKGROUND

Antiseptics are agents designed to kill microbes on exposed surfaces. They are used to prepare the skin for minor and major surgical procedures, to sterilize inanimate articles, operating rooms, hospital environments and for the disinfection of water.

Antiseptics applied to animate bodies are called antiseptics, bactericides, or bacteriostats; those applied to inanimate bodies are called disinfectants or germicides.

Halogen compounds have been used for a long time as antiseptics and disinfectants. Their action and mechanism is exerted by interfering with enzymes and coagulating protein. They are more potent than most local antiseptics.

Among long established preparations are: chloramine T, chloroazodin, Iodoform, tincture of iodine, sodium hypochlorite, hexachlorophene, betadine and halazone. Well-known antibacterial agents that contain chlorine bound to nitrogen are: chloramine T, dichloramine T and halazone. The last compound has been widely used for water disinfection.

None of these N-chloro compounds is a real chloramine in the strict chemical sense; rather, it is a chlorosulfonamide.

Other N-chloro compounds that have been used (or proposed) as antiseptics are the cyclic imides and amidines (see Burger's Medicinal Chemistry, 6th Ed., Part III, Chapter 14).

The present invention relates to novel chloroamino acids which are stable, non-toxic, economic and potent antibacterial agents. Unlike the widely used topical antiseptics such as hexachlorophene and chlorohexidine, these novel chloroamines are non-persistent, i.e., after accomplishing their germicidal or fungicidal action, they are converted into safe, non-toxic materials. Furthermore, they are shown by skin irritation tests to be totally non-irritating in concentration of 1% ($10^4$ ppm). This result is significant as the novel compounds of this invention are active as fungicidal or germicidal agents at concentrations as low as 100 ppm.

Preliminary formulation studies show that the new chloramines are remarkably stable in certain solvents. For example, 2-dichloroamino-2-methyl-1-propyl hemisuccinate showed no decomposition in esters of polyalcohols such as Triacetin at 60° C. for two months. Triacetin is the triacetate of glycerin; it is a viscous liquid with high water solubility and very low toxicity. A concentrated solution of the chloramine in Triacetin suggests itself as a simple, stable antimicrobial product. Of course other aprotic polar solvents can be used as well.

It is desirable that topical antiseptics conform with the following criteria:

(1) the antiseptic should have a broad range of activity against Gram-negative and Gram-positive organisms at low concentrations;

(2) the antiseptic should retain its activity in the presence of soap and protein;

(3) the antiseptic should be non-irritating;

(4) the antiseptic should be stable neat and in solution;

(5) the antiseptic should be non-toxic. The new chloramines of this invention meet all of the above criteria. On the contrary, from a comparative study, all of the products in commercial use fail to meet one or more of the above requirements. Quaternary ammonium compounds are quite active against Gram-positive and Gram-negative organisms but they are easily deactivated by soap and serum. Alcohol, iodine (Betadine), mercurials and silver nitrate tend to irritate and injure the skin. Hexachlorophene is the most widely used phenolic compound employed to disinfect skin and it is compatible with soap. However, it is ineffective against Gram-negative organisms and in animal tests has caused neurotoxicity. Chlorhexidine is a bisguanidine which is generally effective against Gram-positive and Gram-negative oganisms but is deactivated by soap and salts (chlorides, borates, phosphates and sulphate), can cause skin irritation and is not effective against pseudomonas organisms. Chlorine, bromine and iodine are effective antimicrobials but they are irritating and difficult to handle because of their lack of stability.

Alkylcarboxyl derivatives of N-chloroamino alcohols such as 2-chloroamino-2-methyl-1-propyl acetate, i.e.,

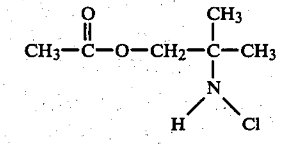

and related compounds are known (U.S. Pat. No. 4,171,452) as antibacterial and antifungal agents in mouth washes. However, they are distinguishable from the N,N-dichloroamino acid derivatives of the present invention by lacking the carboxylic acid function which give the novel compounds of the present invention the following important characteristics:

(1) Increased water solubility;

(2) Partition coefficients having values close to unity which is a value that is very favorable for skin penetration. This ability to penetrate into the skin coupled to high germicidal and fungicidal activity can be exploited in the treatment of acne and topical fungal diseases; and (3) Enhanced germicidal activity. For example, β-dichloroamino-isovaleric acid retains germicidal activity at a concentration of merely 5 ppm or lower.

SUMMARY OF THE INVENTION

The novel chloroamino acids of the present invention are of the structural formula

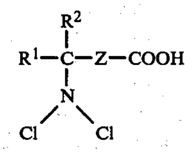

(I)

wherein Z, as a connective structure, can be a variety of structures, as shown below in the Detailed Description Of The Invention, except heteroatoms such as oxygen, nitrogen, and sulfur or moieties containing active hydrogen which will react with the chloroamine within the molecule such as, for example, amino-ethylene or hydroxypropylene.

Similarly, $R^1$ and $R^2$ cannot be hydrogen or any functional groups having a reactive hydrogen.

These chloroamines are unique in that they are stable. This is significant since most known chloroamines, especially of α-amino acids, are extremely unstable, in fact, they decompose often explosively via oxidative decarboxylation.

Needless to say, it is this unique stability which makes it possible for utilizing the novel chloroamines of the present invention as potent antibacterial agents.

Therefore it is an object of the present invention (1) to provide novel antibacterial N,N-dichloro derivatives of amino acids (other than α-amino acids) and the salts thereof; (2) to develop process for the preparation of the novel compounds; (3) to provide methods of application of the novel compounds as topical antiseptics, e.g., germicidal or fungicidal agents; and (4) to provide compositions useful in (a) environmental sanitation of public facilities such as hospitals, schools, and military camps; household; farms, such as dairy or poultry farms;

(b) treatment of food items;

(c) personal hygiene such as skin cleanser, douche product, mouthwash/gargle;

(d) veterinary hygiene such as antiseptic gauze pad; and (e) general surface disinfectant.

DETAILED DESCRIPTION OF THE INVENTION

The present invention concerns novel N,N-dichloro derivatives of an amino acid of the structural formula:

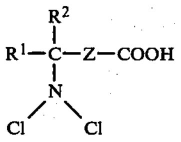

(I)

wherein $R^1$ and $R^2$ are independently (a) loweralkyl especially $C_{1-10}$ linear or branched alkyl such as methyl, ethyl, propyl, isopropyl, isobutyl, amyl, hexyl, heptyl, 3,3-dimethyl, heptyl, or 8,8-dimethyloctyl; or (b) lower cycloalkyl especially $C_{3-10}$ cycloalkyl such as cyclopropyl, cyclopentyl, cyclohexyl, 1-(4-methylcyclohexyl)-, or cyclooctyl;

(c) lower (cycloalkyl-alkyl) especially $C_{4-10}$ (cycloalkyl-alkyl) such as cyclopropylmethyl, cyclopentylethyl or cyclohexylbutyl;

(d) phenyl or lower alkyl-substituted phenyl such as 4-methylphenyl, 3-ethylphenyl, 4-cyclohexylphenyl, or 2,4-dimethylphenyl;

(e) halosubstituted phenyl such as 4-chlorophenyl, 2,4-difluorophenyl, 2,4-dichlorophenyl, 3-bromophenyl, or 4-iodophenyl;

(f) lower alkoxy substituted phenyl especially $C_{1-5}$alkoxy such as 4-methoxyphenyl, 2-ethoxyphenyl, or 4-butoxyphenyl; or (g) phenyl(lower alkyl) especially phenyl $C_{1-5}$ alkyl such as benzyl, 2-phenylethyl, 3-phenylpropyl, 4-phenylbutyl; or $R^1$ and $R^2$ joined together form lower alkylene especially $C_{3-4}$alkylene such as trimethylene ($-CH_2CH_2CH_2-$), tetramethylene ($-CH_2CH_2CH_2CH_2-$) or the like; and Z is (a) lower alkylene especially $C_{1-21}$alkylene such as methylene, ethylene, trimethylene, tetramethylene, heptamethylene, decamethylene, or octadecamethylene (b) $-(CH_2)_n$-phenylene$-(CH_2)_m-$, wherein n and m are independently integers from 0 to 5;

(c) $-(CH_2)_n-\overset{O}{\overset{\|}{C}}-O-$phenylene$-(CH_2)_m$;

(d) $-(CH_2)_{n+1}-O-\overset{O}{\overset{\|}{C}}-$phenylene$-(CH_2)_m-$;

(e) $-(CH_2)_n-\overset{O}{\overset{\|}{C}}-O-(CH_2)_m-$; or (f) $-(CH_2)_{n+1}-O-\overset{O}{\overset{\|}{C}}-(CH_2)_m-$;

(g) $-(CH_2)_{n+1}-O-(CH_2)_m-$ wherein n is an integer from 0–3 and m an integer from 0–20; or a pharmaceutically acceptable base-addition salt thereof.

The preferred embodiment of the present invention comprises compounds of formula (I) wherein $R^1$ and $R^2$ independently are lower alkyl; or alternatively $R^1$ and $R^2$ are joined together to form a lower alkylene; and Z is (a) $C_{1-21}$alkylene;

(b) $-(CH_2)_{n+1}-O-(CH_2)_m-$;

(c) $-(CH_2)_{n+1}O-\underset{\overset{\|}{O}}{C}-(CH_2)_m-$; or (d) $-(CH_2)_n-\underset{\overset{\|}{O}}{C}-O-(CH_2)_{m+1}-$ or a pharmaceutically acceptable salt thereof.

The even more preferred embodiment of the present invention comprises compounds of formula (I) wherein $R^1$ and $R^2$ are independently $C_{1-5}$alkyl such as methyl, ethyl, propyl, butyl or amyl; and Z is (a) $C_{1-3}$alkylene such as methylene, dimethylene, or trimethylene;

(b) $-(CH_2)_{n+1}-O-(CH_2)_m-$, wherein n is an integer from 0 to 3, and m is an integer from 0–10;

(c) $-(CH_2)_{n+1}-\overset{O}{\overset{\|}{O}}-C-(CH_2)_m-$, wherein n and m independently are integers from 0–3;

(d) $-(CH_2)_n-\overset{O}{\overset{\|}{C}}-O-(CH_2)_{m+1}$, wherein n and m independently are integers from 0–3;

or a pharmaceutically acceptable salt thereof.

The most preferred embodiment of the present invention comprises compounds of formula (I) wherein $R^1$ and $R^2$ are methyl; and Z is (a) methylene or dimethylene (b) 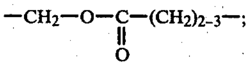 or (c) 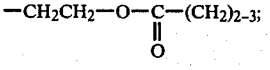

or a pharmaceutically acceptable salt thereof.

The novel compounds of the present invention are prepared from an amino acid of the structural formula:

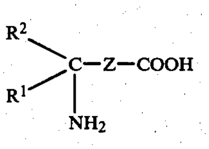

wherein $R^1$ and $R^2$ are as previously defined. The amino acid is treated with a chlorinating agent such as sodium hypochlorite, calcium dihypochlorite, N-chlorosuccinimide together with chlorine, and t-butylhypochlorite in an inert solvent under mild conditions. The preferred solvents are water, alkanols especially $C_{1-5}$alkanols such as methanol, ethanol, isopropanol, propanol, butanol or pentanol, or the combination thereof. Other common solvents such as chloroform, methylenechloride, carbon tetrachloride, diethyl ether, benzene, toluene, cyclohexane or the like may also be used. Of course, the selection of a suitable solvent is limited by the solubility of the amino acid. The chlorination is usually carried out at temperatures about 0° C. to about 50° C., preferably at from about 0° C. to about 25° C. Generally, most chlorinations are substantially complete in about 1 hour to about 24 hours. Under optimal conditions, the reaction takes about 1 to 5 hours.

The starting materials, i.e., the amino acids or their esters are prepared by methods known in the art as illustrated by the following schemes.

(1) Addition of ammonia across a double bond—general procedure for synthesis of β-aminopropanoic acids

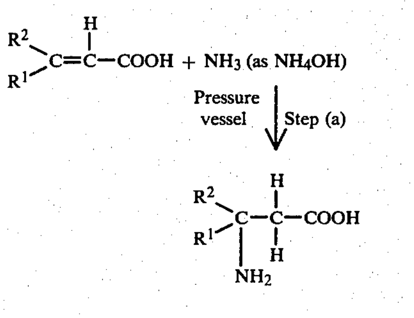

For example, a β,β-disubstituted unsaturated carboxylic acid such as 3,3-dimethylacrylic acid and a sufficient amount of ammonium hydroxide are heated at about 150° in a sealed reactor until the reaction is substantially complete. After cooling, the crude mixture is filtered (if necessary) and then boiled with a sufficient amount of barium hydroxide until evolution of ammonia ceases. The pH of the solution is adjusted to 7 with sulfuric acid and the precipitated barium sulfate is removed by suction filtration. The resultant clear, solution is evaporated to dryness to yield a thick syrup. Treatment of the syrup with dry ethanol and ether yields β,β-dimethyl-β-amino-propanoic acid in pure form.

In the manner substantially the same as described above the following compounds can be made:

(a) β-methyl-β-ethyl-β-aminopropanoic acid from 3-methyl-3-ethylacrylic acid;

(b) β-methyl-β-phenyl-β-aminopropanoic acid from β-methylcinnamic acid (c) β-ethyl-β-phenyl-β-aminopropanoic acid from β-ethylcinnamic acid;

(d) β,β-diphenyl-β-aminopropanoic acid from β-phenylcinnamic acid; and (e) β-cyclohexyl-β-aminopropanoic acid from $\Delta^{1(7)}$-cyclohexene acetic acid.

All the above-mentioned starting materials, i.e., β-disubstituted, unsaturated carboxylic acids (except 3,3-dimethyl acrylic acid, which is commercially available) were synthesized via Reformatsky reactions of ethyl bromoacetate with appropriate ketones. The resultant β-hydroxy esters were than dehydrated and hydrolyzed (or hydrolyzed first, then dehydrated) as shown by the following scheme:

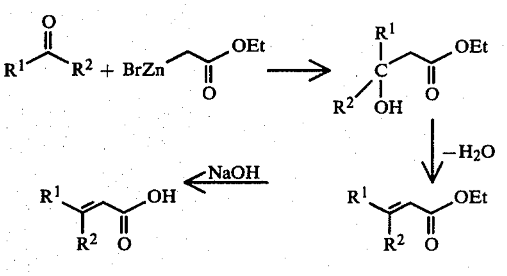

(2) Hydrolysis of 5,5-disubstituted-2-pyrrolidones—preparation of 4,4-disubstituted-4-aminobutanoic acids:

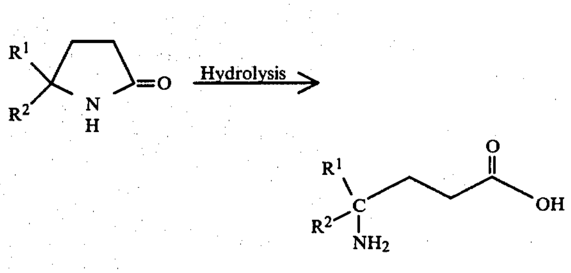

For example, a mixture of 5,5-dimethyl-2-pyrrolidone, an excess amount of barium hydroxide and a sufficient amount of water is heated under reflux until the reaction is substantially complete. The cooled solution is made slightly acidic with sulfuric acid and neutralized with solid barium carbonate or other bases. After removal of solids by filtration, the filtrate is evaporated under reduced pressure to yield a crude product which after three recrystallizations from an inert solvent such as aqueous ethanol gives an analytically pure product of 4-amino-4,4-dimethyl butanoic acid (4-amino-4-methylvaleric acid). 4-amino-2,4-dimethylvaleric acid is prepared similarly from 3,5,5-trimethyl-2-pyrrolidone.

(3) Condensation of an α,α-disubstituted-amino alcohol with a cyclic anhydride-general procedure for the synthesis of compounds of formula (II)

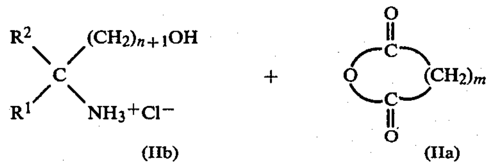

(IIb) (IIa)

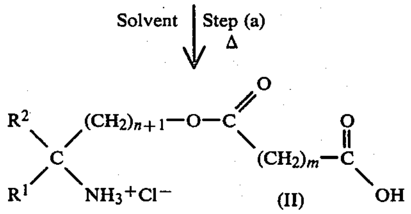

(II)

For example, the compound of formula (II) can be synthesized from an anhydride (IIa) following the above scheme. The anhydride is reacted with the hydrochloride salt of an aminoalcohol (II*b*) in an inert solvent such as toluene or xylene at about 110° C. according to conventional procedures.

Aromatic analogs of compounds (II) such as 2-(2-amino-2,2-dimethylethoxycarbonyl)benzoic acid and other variously substituted aromatic analogs can be prepared in substantially the same manner.

(4) Condensation of an α,α-disubstituted-amino alcohol with an anhydride according to the following scheme—general procedure for the synthesis of compounds of formula (IV).

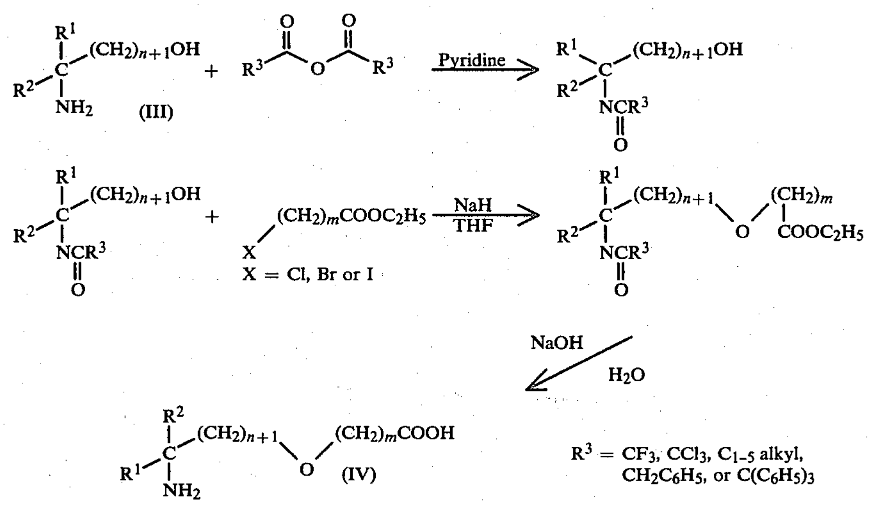

(III) (IV)

For example, an α,α-disubstituted amino alcohol of formula (III) is stirred with an excess of trifluoro-acetic anhydride in pyridine at room temperature until reaction is substantially complete. Excess anhydride and pyridine are removed under reduced pressure. Treatment of the residue with water yields the N-protected amino alcohol. The N-protected amino alcohol is alkylated at the oxygen (using sodium hydride in tetrahydrofuran) with the appropriate halo-ester. Basic hydrolysis of the amide and ester functions in the alkylated materials yields the amino acids of generic formula (IV)

(5) General Procedure for the synthesis of compounds of formula V or VI according to the following scheme:

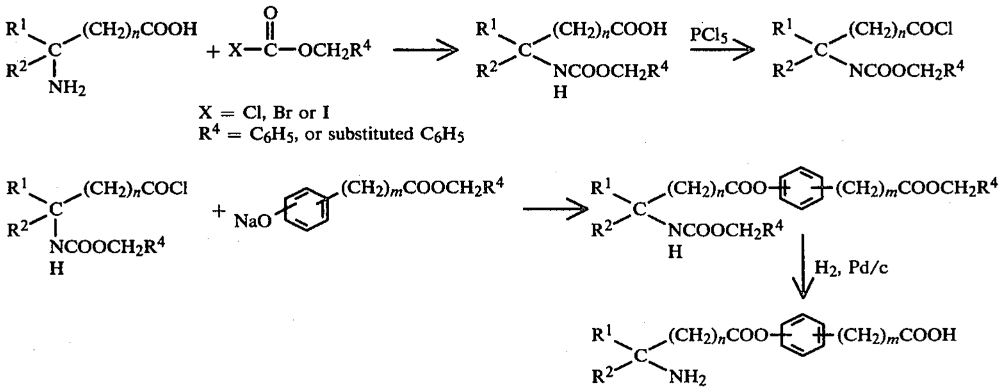

-continued

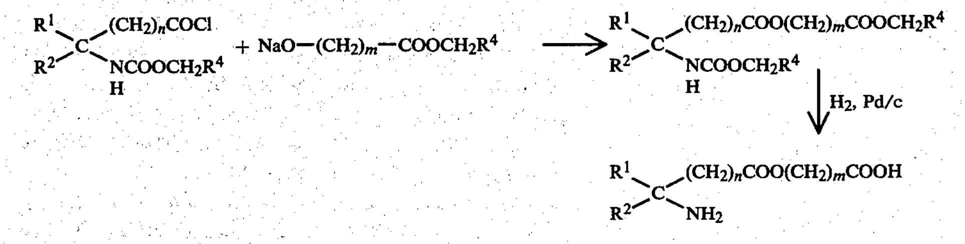

The appropriate amino acid is protected as the N-carbobenzyloxy derivative. The acid is converted to the acyl chloride which is then reacted with the alkali metal salt of the appropriate phenol or alcohol. Catalytic hydrogenation is then used to remove in a single step the benzyl ester and the N-carbobenzyloxy protective group.

The pharmaceutically acceptable salts of the novel compounds of this invention are prepared from neutralizing the subject acids with an inorganic base. The mostly employed bases are sodium hydroxide, potassium hydroxide, calcium hydroxide, and lithium hydroxide. Usually, the neutralization is conducted in an inert solvent such as water, a $C_{1-3}$ alkanol such as methanol, ethanol or isopropanol, acetone, tetrahydrofuran, dioxane and acetonitrile or a combination thereof. Under normal circumstances, the salt-formation process is carried out in water or aqueous ethanol at 0°-75° C., preferably at 0° C.-25° C., followed by crystallization and filtration.

The unique characteristic of the chloramines of this invention is their superior stability in aqueous media as compared to other known chloramines. It is discovered that an increase of the separation distance (Z) between the carboxylic acid (—COOH) and the chloroamine moiety ($—NCl_2$) leads to chemical entities that are progressively more stable. The effect of this distance on stability in aqueous medium is illustrated in the following table.

Stability ($t_{1/2}$) of some chloroamino acids in pH 4 Acetate Buffer at 34° C.

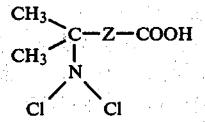

| | |
|---|---|
| Z = nothing | $t_{1/2}$ = 0 (violent decomposition) |
| Z = $—CH_2—$ | $t_{1/2}$ = 29 hours |
| Z = $—CH_2CH_2—$ | $t_{1/2}$ = 57 days |
| 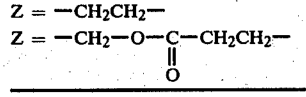 | $t_{1/2}$ = 300 days |

It is significant that a chloramine be stable enough to allow the exploitation of its high germicidal and fungicidal activity in the treatment of acne and topical fungal diseases.

The novel chloramines of the present invention have shown germicidal activity at concentrations as low as about 1-100 ppm (part per million) and fungicidal activity at a concentration as low as about 10 to 1,000 ppm. Skin irritation tests performed with some of the representative compounds indicate that they are totally non-irritating at concentrations up to 1% (10,000 ppm) in buffered aqueous media.

The compounds of this invention are preferably applied as a solution (normally, 1-95%, but preferably 5-25%) in water. The term "solution" is meant to include a water-miscible alcohol solution, such as isopropyl alcohol or ethyl alcohol, or the alcohol may be used undiluated. The solution is applied in any suitable manner, e.g., by spraying or swabbing the affected area. Alternatively, the compounds of this invention may be applied in the form of any topical pharmaceutical form, such as a powder, paste, salve, ointment, aerosol spray, etc. These compounds can also be dissolved in a cosmetic base, a cream or oil, and added to other solutions or sprays normally applied to the skin, such as insect repellants, sun screen lotions and ointments and creams normally used in the treatment of skin rashes and allergies, and in topical anesthetics used for the relief of pain and itching of sunburn. The skilled artisan concerned with the subject matter of this invention can easily prepare any of the above-mentioned conventional pharmaceutical dosage forms for topical application by simply referring to "REMINGTON'S PHARMACEUTICAL SCIENCES" (Fourteenth Edition), 1970, pp. 1461-1762.

Normally, a single application brings immediate relief to the area treated; however, for stubborn cases, repeated application may be necessary.

Without further elaboration, it is believed that one of ordinary skill in the art can, using the preceeding description, utilize the present invention to its fullest extent. The following preferred specific embodiments are, therefore, to be construed as merely illustrative and not limitative of the remainder of the specification and claims in any way whatsoever.

EXAMPLE 1

The Preparation of 2-dichloroamino-isovaleric acid (II)

β-Amino-isovaleric acid (4.97 g, 42.43 mmol) is dissolved in 100 ml of methanol to give a slightly yellow solution; t-butyl hypochlorite (9.2 g, 84.86 mmol) is then added slowly via pipette away from direct light. Addition is complete in 10 min. The solution is stirred for 2 hr, then the slight colloidal precipitate that had formed is removed by filtration. The solvents are evaporated without heating to more than 35° C. After drying under vacuum, there is obtained 7.50 g (95% yield) of white crystalline material with a tinge of green; mp 44°-46° C.; NMR ($CD_3OD$) 2.83 (s, 2H, $CH_2$), 1.58 (s, 6H, $CH_3$).

Anal. Calcd for $C_5H_9NCl_2O_2$ (185.95): C, 32.29; H, 4.84; N, 7.53. Found: C, 32.58; H, 4.70; N, 7.50.

EXAMPLE 2

The Preparation of 4-Dichloroamino-4-methylvaleric acid (III)

4-Amino-4-methylvaleric acid (2 g, 15.26 mmol) is suspended in good grade methanol. After cooling to 0°

C. t-butyl hypochlorite (3.31 g, 30.52 mmol) is added via pipette over 5 minutes. Almost everything dissolves. The mixture is stirred for 2 hr at 0° C. and then allowed to warm to room temperature. Filtration through Celite is followed by evaporation of the methanol on the rotary evaporator at 30° C. The residue is taken up in dichloromethane and the insoluble solid material is removed by filtration. Evaporation of the dichloromethane yields a yellow oil that crystallizes on cooling: mp 35°-38° C.

Anal. Calcd for $C_6H_{11}NO_2Cl_2$ (199.96): C, 36.03; H, 5.50; N, 7.00. Found: C, 36.61; H, 5.60; N, 6.85.

EXAMPLE 3

The Preparation of 2-Dichloroamino-2-methylpropylhemisuccinate (IV)

2-Amino-2-methyl-1-propanol hydrochloride (5 g, 40 mmol) and succinic anhydride (4.2 g, 42 mmol), are suspended in 50 ml of toluene. The reaction mixture is heated under reflux for 24 hr. The toluene is decanted, the residue is taken up in water and added slowly to 150 ml of chlorox (0.7 M) at 0° C. The mixture is extracted 3 times with dichloromethane. The aqueous layer is then acidified with 5 N HCl and extracted 3 times with dichloromethane. The combined organic layers are dried over sodium sulfate. Evaporation of the solvent yields a yellow oil (6.1 g, 59% yield) that is chromatographed on silica gel (15% EtOAc-$CH_2Cl_2$ as eluent).

NMR ($CDCl_3$): 1.39 (s, 6H), 2.68 (s, 4H), 4.22 (s, 2H); 9.39 (s, 1H).

IR (neat): 3000, 1740 and 1710 $cm^{-1}$.

Anal. Calcd for $C_7H_{13}NCl_2O_4$: C, 37.23; H, 5.08; N, 5.43 Found: C, 37.18; H, 5.20; N, 5.10

EXAMPLE 4

The Preparation of 2-dichloramino-2-methylpropyl-hemiglutarate (V)

A suspension of 2-amino-2-methyl-1-propanol hydrochloride (0.5 gm; 4 mmole) and 0.48 gm of glutaric anhydride in toluene (20 ml) is refluxed for 16 hrs. After cooling to room temperature, the toluene is decanted. The glassy residue is reconstituted with 10 ml of water and added to 30 ml of chlorox (0.7 M) which is chilled in an ice-water bath.

The reaction mixture is allowed to stir at 0° C. for 5 min. Organic impurities are removed by extracting the reaction mixture with $CH_2Cl_2$ three times. The chlorox solution is then acidified with 5 M HCl and extracted with $CH_2Cl_2$ twice. The organic layer is collected and dried over anhydrous sodium sulfate. The solvent is evaporated under reduced pressure and the residue (0.52 g) is further purified by chromatography (silica gel) eluting with 15% EtOAc-$CH_2Cl_2$.

NMR ($CDCl_3$): 1.39 (s, 6H); 1.97 (m, 2H); 2.3-2.6 (m, 4H); 4.21 (s, 2H); 10.40 (s, 1H).

IR (neat): 1740 $cm^{-1}$, 1720 $cm^{-1}$.

Anal. Calcd. for $C_8H_5NCl_2O_4$: N, 5.15; C, 39.72; H, 5.56. Found: N, 4.98; C, 39.90; H, 5.60.

EXAMPLE 5

The preparation of 6-Dichloroamino-6-methyl-heptanoic acid (VI)

6-Amino-6-methyl heptanoic acid (1.19 g, 7.48 mmol) is dissolved in ~80 ml of MeOH. To the solution at 0° C. (ice bath) is added t-butyl-hypochlorite (1.62 g, 14.96 mmol) via a Pasteur pipette. After stirring for 1 hour at 0° C., the mixture is allowed to reach room temperature. The slightly cloudy solution is filtered through syntered glass and the solvent is removed under vacuum (do not heat above 35° C.). The residue is dissolved in dichloromethane and the solid is removed by filtration. Upon evaporation of the dichloromethane, the dichloroamine is obtained (95% yield) as a green oil.

Anal. Calcd for $C_8H_{15}NCl_2O_2$ C, 42.14; H, 6.57; N, 6.14. Found: C, 42.19; H, 6.51; N, 6.08.

The starting material, 6-amino-6-methylheptanoic acid has four methylene units between the tertiary carbon and the carboxylic acid function. It has been synthesized by the following path:

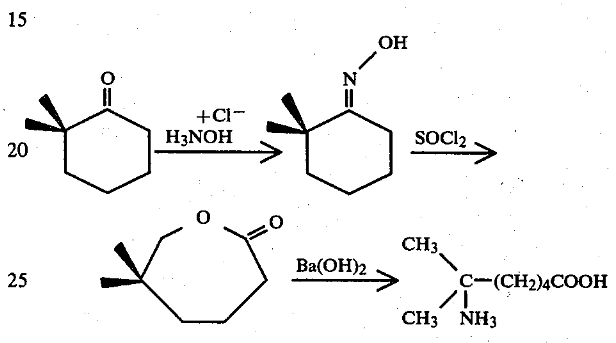

1-1-Dimethylcyclohexanone is treated with hydroxylamine hydrochloride to give the oxime. The latter is transformed (via Beckmann rearrangement) into the gem-dimethyl caprolactam. Basic hydrolysis of the lactam gives the amino acid.

EXAMPLE 6

The Preparation of the Sodium Salt of 2-Dichloroamino-2-methylpropyl hemisuccinic acid 2-Dichloroamino-2-methylpropyl hemisuccinic acid (2 g) is dissolved in 10 ml of methanol. To the solution is added 21 ml of a 0.37 M solution of sodium methoxide in methanol. After stirring for a few minutes, the solvent is removed under reduced pressure. Further removal of the methanol is accomplished by formation of the azeotrope with benzene until the residue starts to solidify. The white solid residue is further purified by recrystallization from acetonitrile to afford 2.0 g of white, fluffy crystals of sodium 2-dichloroamino-2-methylpropyl hemisuccinate.

Anal. Calcd for $C_7H_{12}NCl_2O_4Na$: C, 34.31; H, 4.32; N, 5.00. Found: C, 34.57; H, 4.30; N, 4.90.

EXAMPLE 7

The Preparation of the Sodium Salt of 2-Dichloroamino-2-methylpropyl hemiglutaric acid 2-Dichloroamino-2-methylpropyl hemiglutaric acid (1 g) is dissolved in 10 ml of methanol and a solution of sodium methoxide in methanol (15 ml, 0.35 M) is added. After stirring for 10 minutes, the methanol is thoroughly removed by azeotropic evaporation with benzene until the residue solidifies. The solid is recrystallized from a mixture of acetonitrile and methanol, to afford 0.7 g of white crystals.

Anal. Calcd for $C_8H_{14}NCl_2O_4Na$: C, 36.75; H, 4.80; N, 4.76. Found: C, 37.10; H, 4.88; N, 4.34.

EXAMPLE 8

Contact Germicidal Activity of Chloramines Cultures and Media

The organisms used in the contact germicidal screen are all maintained as stock cultures on nutrient agar slants at 4° C. They are transferred and biochemically diagnosed monthly. The five organisms used are:

| | |
|---|---|
| *Staphylococcus aureus* | ATCC No. 6538 |
| *Staphylococcus epidermis* | ATCC No. 12228 |
| *Bacillus cereus* | ATCC No. 6051-1 |
| *Salmonella typhimurium* | ATCC No. 13311 |
| *Pseudamonas aeruginosa* | ATCC No. 14502 |

The media used are: Nutrient Agar BBL No. 11472, Tryptose Phosphate Broth Difco No. 0060-01, Nutrient Broth Difco No. 0003-01, TC Horse Serum Dessicated Difco No. 5537-72 restored with 100 ml of sterile distilled water.

PROCEDURE

Overnight cultures of the test organisms are grown in tryptose phosphate broth. After 15–16 hours, the cultures are centrifuged at 45,000 RPM for 15 minutes, and the supernatant replaced with fresh warm (37° C.) media. After two hours of incubation, the absorbance of the culture at 650 nm is determined and diluted with nutrient broth to $1\times10^7$ colony forming units per ml (using a previous determined standard curve: colony forming units/ml vs. absorbance at 650). The diluted cultures are maintained at 4°–8° C. throughout the screen.

The compounds are weighed into sterile 100 ml volumetric flasks, and immediately before screening dissolved in one of the following buffers: 0.1 M NaOAc pH 4.6 or 0.1 M $NaH_2PO_4$ pH 7.0. If solubility poses a problem, 10–30% methanol is used to effect solution. Two denaturing agents are also tested: TC Dessicated Horse Serum restored with 100 ml distilled water and 10% Trition$\times$100. When used, 2.5 ml of the denaturing agent is mixed with 2.5 ml of double strength test solution thirty minutes before the bacterial suspension is added.

The screen is initiated when 0.2 ml of the bacterial suspension is added to 5.0 ml of the test solution contained in a sterile 25 ml glass stoppered flask. At intervals of 0.5, 2.5, 5.0, 10.0 and 15.0 minutes, a loopful of the inoculated test solution is subcultured into 5 ml of sterile nutrient broth and mixed with a vortex, the high dilution serving to stop the action of the compound. All of the subculture tubes are incubated at 37° C. and checked for signs of growth by turbidity at 1, 3, 5 and 7 days. The earliest subculture time at which no growth is present is considered the endpoint and is recorded as the sterilization time.

CONTROLS

An aliquot of 0.2 ml of the diluted culture is transferred to 5 ml of buffer to simulate 0.2 ml in 5 ml of test solution.

(a) Purity: A loopful of the inoculated buffer is streaked onto nutrient agar to check colony morphology and lack of contaminants.

(b) Viability: A loopful of the inoculated buffer is subcultured to 5 ml of nutrient broth as in the screen and incubated at 37° C. for 24 hours.

(c) Dilution of the Test Solution: A loopful of the test solution is transferred to a 5 ml tube of nutrient broth, and a loopful of the inoculated buffer is transferred to the same tube of broth. Turbidity after 24 hours at 37° C. indicates that the dilution of the test solution in the nutrient broth subculture tubes during the screen is great enough to stop the action of the compound.

(d) Purity of Organisms in the Test Solution: After the 15 minute subculture, a loopful of the inoculated test solution is streaked onto nutrient agar to insure that contamination has not occurred during the screen.

(e) lack of Bactericidal Activity of Buffers and Other Solvents: Before a buffer or other solvent is used as a diluent, it is screened against the five organisms to insure that the buffer or solvent has no antibacterial activity itself.

TABLE I

Contact Germicidal Profile of 2-Dichloroamino-isovaleric acid (II) Sterilization Time Against Five Test Organisms[a]

| Buffer and/or Denaturants Used | Compound Concentration (PPM) | Sterilization Time (minutes) S.a | S.e. | B.s. | S.t. | P.a. |
|---|---|---|---|---|---|---|
| 0.1M NaOAc pH 4.6 | 1014.8 | 0.5 | 0.5 | 0.5 | 0.5 | 0.5 |
| | 298.9 | 0.5 | 0.5 | 0.5 | 0.5 | 0.5 |
| | 104.7 | 0.5 | 0.5 | 0.5 | 0.5 | 0.5 |
| | 71.7 | 0.5 | 0.5 | 0.5 | 0.5 | 0.5 |
| | 32.1 | 2.5 | 2.5 | 0.5 | 0.5 | 2.5 |
| | 12.2 | 2.5 | 2.5 | 2.5 | 0.5 | 2.5 |
| | 10.0 | 2.5 | 5.0 | 2.5 | 0.5 | 2.5 |
| | 10.0+ | 2.5 | 2.5 | 2.5 | 0.5 | 2.5 |
| | 4.5 | 10.0 | 10.0 | 2.5 | 2.5 | 5.0 |
| | 1.8 | 15.0 | 15 | 5.0 | 5.0 | 15 |
| 0.1M $NaH_2PO_4$ pH 7.0 | 1016.0 | 2.5 | 2.5 | 0.5 | 0.5 | 2.5 |
| | 316.6 | 5.0 | 10.0 | 2.5 | 2.5 | 5.0 |
| | 107.8 | 10.0 | 15.0 | 5.0 | 2.5 | 15 |
| Serum[b]: 4.6 Buffer 1:1 | 1001.2 | 0.5 | 0.5 | 0.5 | 0.5 | 2.5 |
| | 304.6 | 15 | 15 | 2.5 | 2.5 | 15 |
| | 51.0 | 15 | 15 | 15 | 15 | 15 |
| pH 4.6 Buffer with | | | | | | |
| 10% Serum | 300 | 0.5 | 0.5 | 0.5 | 0.5 | 0.5 |
| 20% Serum | 300 | 2.5 | 2.5 | 0.5 | 0.5 | 2.5 |
| 35% Serum | 300 | 10.0 | 15.0 | 2.5 | 2.5 | 10.0 |
| 25% Serum | 899.25 | 0.5 | 0.5 | 0.5 | 0.5 | 0.5 |
| 33% Serum | 606.9 | 0.5 | 0.5 | 0.5 | 0.5 | 2.5 |
| Triton X100[c]: 4.6 buffer 1:1 | 304.8 | 0.5 | 0.5 | 0.5 | 0.5 | 0.5 |
| | 51.0 | 2.5 | 2.5 | 0.5 | 0.5 | 2.5 |

[a]*S.a.* = *Staphylococcus aureus* ATCC No. 6538
*S.e.* = *Staphylococcus epidermidis* ATCC No. 12228
*B.s.* = *Bacillus subtilis* ATCC No. 6051-1
*S.t.* = *Salmonella typhimurium* ATCC No. 13311
*P.a.* = *Pseudamonas aeruginosa* ATCC NO. 14502
[b]Serum = TC Horse Serum Dessicated Difco 5357-72 restored with 100 milliliters of Distilled $H_2O$.
[c]Triton X100 = 10% Solution in Distilled $H_2O$.
+Screened simultaneously with four other compounds.

TABLE II

Contact Germicidal Profile of 4-Dichloroamino-methylvaleric acid (III)

Sterilization Time Against Five Test Organisms[a]

| Buffer and/or Denaturants Used | Compound Concentration (PPM) | Sterilization Time (minutes) S.a | S.e. | B.s. | S.t. | P.a. |
|---|---|---|---|---|---|---|
| 0.1M NaOAc pH 4.6 | 1007.7 | 0.5 | 0.5 | 0.5 | 0.5 | 0.5 |
| | 102.2 | 2.5 | 0.5 | 0.5 | 0.5 | 0.5 |
| | 9.6 | 10.0 | 5.0 | 2.5 | 2.5 | 5.0 |
| | 10.0+ | 5.0 | 10.0 | 2.5 | 2.5 | 2.5 |
| 0.1M $NaH_2PO_4$ pH 7.0 | 1012.3 | 5.0 | 5.0 | 2.5 | 0.5 | 5.0 |
| | 103.5 | 15 | 15 | 10.0 | 5.0 | 15 |
| | 9.7 | 15 | 15 | 15 | 15 | 15 |
| Serum[b]: 4.6 Buffer 1:1 | 1000.0 | 0.5 | 2.5 | 0.5 | 0.5 | 5.0 |
| | 308.0 | 5.0 | 10.0 | 2.5 | 2.5 | 15 |

TABLE II-continued

Contact Germicidal Profile of 4-Dichloroamino-methylvaleric acid (III)

Sterilization Time Against Five Test Organisms[a]

| Buffer and/or Denaturants Used | Compound Concentration (PPM) | Sterilization Time (minutes) S.a | S.e. | B.s. | S.t. | P.a. |
|---|---|---|---|---|---|---|
| Triton X100[c]: 4.6 buffer 1:1 | 308.0 | 2.5 | 2.5 | 0.5 | 0.5 | 2.5 |

[a]S.a. = *Staphylococcus aureus* ATCC No. 6538
S.e. = *Staphylococcus epidermidis* ATCC No. 12228
B.s. = *Bacillus subtilis* ATCC No. 6051-1
S.t. = *Salmonella typhimurium* ATCC No. 13311
P.a. = *Pseudamonas aeruginosa* ATCC NO. 14502
[b]Serum = TC Horse Serum Dessicated Difco 5357-72 restored with 100 milliliters of Distilled $H_2O$.
[c]Triton X100 = 10% Solution in Distilled $H_2O$.
+Screened simultaneously with four other compounds.

TABLE III

Contact Germicidal Profile of 2-Dichloroamino-2-methyl-1-propyl hemisuccinate (IV) Sterilization Time Against Five Test Organisms[a]

| Buffer and/or Denaturants Used | Compound Concentration (PPM) | Sterilization Time (minutes) S.a | S.e. | B.s. | S.t. | P.a. |
|---|---|---|---|---|---|---|
| 0.1M NaOAc pH 4.6 | 1008.0 | 0.5 | 0.5 | 0.5 | 0.5 | 0.5 |
| | 106.2 | 2.5 | 2.5 | 2.5 | 0.5 | 2.5 |
| | 8.6 | 15.0 | 15.0 | 5.0 | 5.0 | 10.0 |
| | 10.0+ | 15 | 10.0 | 2.5 | 2.5 | 5.0 |
| 0.1M $NaH_2PO_4$ pH 7.0 | 1070.3 | 10.0 | 10.0 | 2.5 | 0.5 | 15 |
| | 149.7 | 10.0 | 15 | 10.0 | 15.0 | 15 |
| | 9.8 | 15 | 15 | 15 | 15 | 15 |
| Serum[b]: 4.6 Buffer 1:1 | 1024.0 | 2.5 | 2.5 | 0.5 | 2.5 | 10.0 |
| | 338.7 | 15.0 | 15 | 5.0 | 10.0 | 15 |
| Triton X100[c]: 4.6 buffer 1:1 | 308.0 | 2.5 | 2.5 | 0.5 | 0.5 | 2.5 |

[a]S.a. = *Staphylococcus aureus* ATCC No. 6538
S.e. = *Staphylococcus epidermidis* ATCC No. 12228
B.s. = *Bacillus subtilis* ATCC No. 6051-1
S.t. = *Salmonella typhimurium* ATCC No. 13311
P.a. = *Pseudamonas aeruginosa* ATCC NO. 14502
[b]Serum = TC Horse Serum Dessicated Difco 5357-72 restored with 100 milliliters of Distilled $H_2O$.
[c]Triton X100 = 10% Solution in Distilled $H_2O$.
+Screened simultaneously with four other compounds.

TABLE IV

Contact Germicidal Profile of 2-Dichloroamino-2-methyl-1-propyl hemiglutarate (V) Sterilization Time Against Five Test Organisms[a]

| Buffer and/or Denaturants Used | Compound Concentration (PPM) | Sterilization Time (minutes) S.a. | S.e. | B.s. | S.t. | P.a. |
|---|---|---|---|---|---|---|
| 0.1M NaOAc pH 4.6 | 911.8 | 0.5 | 0.5 | 0.5 | 0.5 | 0.5 |
| | 99.1 | 2.5 | 2.5 | 2.5 | 0.5 | 2.5 |
| | 10.0 | 10.0 | 10.0 | 5.0 | 5.0 | 10.0 |
| | 10.0+ | 10.0 | 10.0 | 2.5 | 2.5 | 5.0 |
| 0.1M $NaH_2PO_4$ pH 7.0 | 1024.4 | 5.0 | 10.0 | 2.5 | 5.0 | 15 |
| | 106.7 | 15 | 15 | 10.0 | 15 | 15 |
| | 10.0 | 15 | 15 | 15 | 15 | 15 |
| Serum[b]: 4.6 Buffer 1:1 | 1042.0 | 2.5 | 2.5 | 0.5 | 2.5 | 10.0 |
| | 291.4 | 15 | 15 | 5.0 | 10.0 | 15 |
| Triton X100[c]: 4.6 | 291.4 | 2.5 | 2.5 | 0.5 | 0.5 | 2.5 |

TABLE IV-continued

Contact Germicidal Profile of 2-Dichloroamino-2-methyl-1-propyl hemiglutarate (V) Sterilization Time Against Five Test Organisms[a]

| Buffer and/or Denaturants Used | Compound Concentration (PPM) | Sterilization Time (minutes) S.a. | S.e. | B.s. | S.t. | P.a. |
|---|---|---|---|---|---|---|
| buffer 1:1 | | | | | | |

[a]S.a. = *Staphylococcus aureus* ATCC No. 6538
S.e. = *Staphylococcus epidermidis* ATCC No. 12228
B.s. = *Bacillus subtilis* ATCC No. 6051-1
S.t. = *Salmonella typhimurium* ATCC No. 13311
P.a. = *Pseudamonas aeruginosa* ATCC NO. 14502
[b]Serum = TC Horse Serum Dessicated Difco 5357-72 restored with 100 milliliters of Distilled $H_2O$.
[c]Triton X100 = 10% Solution in Distilled $H_2O$.
+Screened simultaneously with four other compounds.

TABLE V

Summary of Germicidal Activity of Compounds (II)-(V)

| Concentration[a] (PPM) | Compound No. | Sterilization Time (minutes) Against Five Test Organisms[b] S.a. | S.e. | B.s. | S.t. | P.a. |
|---|---|---|---|---|---|---|
| 1000 | (II) | 0.5 | 0.5 | 0.5 | 0.5 | 0.5 |
| | (III) | 0.5 | 0.5 | 0.5 | 0.5 | 0.5 |
| | (IV) | 0.5 | 0.5 | 0.5 | 0.5 | 0.5 |
| | (V) | 0.5 | 0.5 | 0.5 | 0.5 | 0.5 |
| 100 | (II) | 0.5 | 0.5 | 0.5 | 0.5 | 0.5 |
| | (III) | 2.5 | 0.5 | 0.5 | 0.5 | 0.5 |
| | (IV) | 2.5 | 2.5 | 2.5 | 0.5 | 2.5 |
| | (V) | 2.5 | 2.5 | 2.5 | 0.5 | 2.5 |
| 10 | (II) | 2.5 | 2.5 | 2.5 | 0.5 | 2.5 |
| | (III) | 5.0 | 10.0 | 2.5 | 2.5 | 2.5 |
| | (IV) | 15 | 10.0 | 2.5 | 2.5 | 5.0 |
| | (V) | 10.0 | 10.0 | 2.5 | 2.5 | 5.0 |
| 1000 with 50% Horse Serum | (II) | 0.5 | 0.5 | 0.5 | 0.5 | 2.5 |
| | (III) | 0.5 | 2.5 | 0.5 | 0.5 | 5.0 |
| | (IV) | 2.5 | 2.5 | 0.5 | 2.5 | 10.0 |
| | (V) | 2.5 | 2.5 | 0.5 | 2.5 | 10.0 |
| 300 with 50% Horse Serum | (II) | 15 | 15 | 2.5 | 2.5 | 15 |
| | (III) | 5.0 | 10.0 | 2.5 | 2.5 | 15 |
| | (IV) | 15.0 | 15 | 5.0 | 10.0 | 15 |
| | (V) | 15 | 15 | 5.0 | 10.0 | 15 |
| 300 with 50% Triton X100 | (II) | 0.5 | 0.5 | 0.5 | 0.5 | 0.5 |
| | (III) | 2.5 | 2.5 | 0.5 | 0.5 | 2.5 |
| | (IV) | 2.5 | 2.5 | 0.5 | 0.5 | 2.5 |
| | (V) | 2.5 | 2.5 | 0.5 | 0.5 | 2.5 |

[a]All compounds dissolved in 0.1M NaOAc pH 4.6 buffer.
[b]S.a. = *Staphylococcus aureus* ATCC No. 6538
S.e. = *Staphylococcus epidermidis* ATCC No. 12228
B.s. = *Bacillus subtilis* ATCC No. 6051-1
S.t. = *Salmonella typhimurium* ATCC No. 13311
P.a. = *Pseudamonas areuginosa* ATCC NO. 14502

EXPERIMENT 9

Fungicidal Activity in Chloramines

Cultures and Media:

The organisms used in the Contact Fungicidal Screen are a dermatophyte, trychophyton mentagrophytes, frequently associated with athlete's foot; a yeast, *Candida albican,* causative agent of thrush and vaginitis; a phycomycete, *Rhizopus oryzae,* commonly known as black bread mold; an ascomycete, *Aspergillus fumagatis,* found in chicken droppings and causing lung infections; and another dermatophyte, *Microsporum canis,* which causes ringworm. These organisms are maintained as stock cultures at 4° C. on agar slants of the following composition: dextrose 2%, Neopeptone (Difco) 1%, agar 2%. Fluid medium of the same nutrient composition (without agar) was used to test the viability of the organisms after exposure to the fungicide. This medium is also known as Sabouraud's medium.

The *Trychophyton mentagrophytes* is grown in Sabouraud's liquid medium in 100 ml dilution bottles with sufficient glass beads to rise just above the surface of the medium. Incubation is at 30° C. for five to seven days or until such time when aerial growth assures the presence of adequate sporulation. At the end of the incubation period a rubber stopper is substituted for the cotton plug and the bottle is shaken in the horizontal position on a Kahn shaker 15 minutes. Ten ml of the suspension is transferred to a sterile 15 ml tube and centrifuged at 1000 rpm for five minutes. This assures that all mycelial fragments and clumped spores are removed from the suspension. Five ml of the supernate are removed to a sterile tube for use in testing fungicidal activity.

The *Candida albican* is grown in Sabouraud's liquid medium at 25°-30° C. for three days. At the end of the incubation period the cell suspension is centrifuged at 200 G and washed with sterile physiological saline (0.85% NaCl). The density of the cell suspension is determined by counting in a hemacytometer. The suspension is stored a 4° C. until it is used, at which time it is diluted with sterile physiological saline to a density of $5\times10^6$ cells per ml.

A Sabouraud's agar plate culture of *Rhizopus oryzae* is prepared by planting an inoculum at the center of the agar plate and incubating the culture at 25°-30° C. for three to five days. The mycelial mat is removed from the surface of the agar using a sterile spatula. It is transferred to a heat sterilized glass tissue grinder and macerated with 25 ml of sterile physiological saline. The suspension is then filtered through sterile glass wool. The density of the sporangia spore suspension is determined by counting in a hemacytometer. The suspension is stored at 4° C. until it was used, at which time it was diluted with sterile physiological saline to a density of $5\times10^6$ spores per ml.

Sabouraud's agar plate cultures of *Aspergillus fumigatus, Microsporum canis,* and a different culture of *Trychophyton mentagrophytes* are prepared by planting an inoculum at the center of an agar plate and incubating at 25°-30° C. for seven to ten days. The mycelial mats are removed from the surface of the agar and prepared in the same manner as the Rhizopus culture.

Procedure:

The compounds are weighed into heat sterilized 100 ml volumetric flasks and immediately before screening dissolved in 0.1 M NaOAc pH 4.6 buffer (test solutions).

The broth culture of *Trychophyton mentagrophytes* and the test solutions are held for a minimum of 15 minutes in a 20° C. water bath prior to the exposure, so that the temperature is constant. Five tenths (0.5) ml of the broth spore suspension is added to 5 ml of the test solution and thoroughly mixed. At intervals of 0.5 minute, 1 minute, 2 minutes, and 5 minutes, 0.1 ml aliquots of the suspension of the spores in the test solution are removed and immediately transferred to flasks containing 200 ml of sterile Sabouraud's liquid medium. A control flask is first inoculated with 0.1 ml of the test solution, shaken well and then inoculated with 0.1 ml of the spore suspension to insure that the dilution factor of the broth is beyond any fungistatic activity of the test solution. The flasks are then incubated at 30° C. for ten days with daily observation for mycelial growth.

The Aspergillus, Candida, Microsporum and Rhizopus species are screened in a slightly different manner. Basically, the procedure for the Contact Germicidal Efficiency Screen is utilized. After the test solutions are made up, 5 ml aliquots are pipetted into heat sterilized 25 ml glass stoppered erlenmeyer flasks. The screen is initiated when 0.5 ml of the $5\times10^6$ cell (spore) per ml suspension is added to the flask containing 5 ml of the test solution. At intervals of 0.5, 2.5, 5.0, 10.0 and 15.0 minutes, a 4 mm loopful of the inoculated test solution is subcultured into 7 mL of sterile fluid Sabouraud's medium and mixed on a vortex, the high dilution serving to stop the action of the compound. The subculture tubes are incubated at 25°-30° C. for ten days with daily observation for mycelial growth. The earliest subculture time at which no growth is present is considered the endpoint and is recorded as the sterilization time.

To insure the viability of the culture, a 0.5 ml aliquot of the $5\times10^6$ cells (spores) per ml suspension is transferred to 5 ml of the pH 4.6 buffer. A loopful of the inoculated buffer is then subcultured to 7 ml of fluid Sabouraud's medium and incubated at 25°-30° C. for ten days. To insure that the dilution of the test solution into the subculture medium does stop the action, a loopful of the test solution and a loopful of the inoculated buffer are transferred into the same subculture tube. This tube is also incubated at 25°-30° C. for ten days. The results are summarized below in Table VI.

TABLE VI

Sterilization Time Against Five Test Organisms[a]

| Compound | Compound concentration (PPM) | Sterilization Time (min) *A.f.* | *C.a.* | *M.c.* | *R.o.* | *T.m.* |
|---|---|---|---|---|---|---|
| (II) | 1000 | 15 | 2.5 | 2.5 | 10.0 | 0.5 |
| | 100 | 15 | 15 | 10.0 | 15 | 0.5 |
| | 10 | 15 | 15 | 15 | 15 | 5.0 |
| (III) | 1000 | 10.0 | 0.5 | 0.5 | 10.0 | 0.5 |
| | 100 | 15 | 15 | 5.0 | 15 | 0.5 |
| | 10 | 15 | 15 | 15 | 15 | 5.0 |
| (IV) | 1000 | 15 | 2.5 | 2.5 | 15 | 0.5 |
| | 100 | 15 | 15 | 15.0 | 15 | 2.5 |
| | 10 | 15 | 15 | 15 | 15 | 5.0 |
| (V) | 1000 | 15 | 0.5 | 2.5 | 15 | 0.5 |
| | 100 | 15 | 15 | 5.0 | 15 | 2.5 |
| | 10 | 15 | 15 | 15 | 15 | 5.0 |
| (VI) | 1000 | 5.0 | 0.5 | 0.5 | 15 | |
| | 100 | 15 | 2.5 | 2.5 | 15 | |
| | 10 | 15 | 15 | 10.0 | 15 | |

[a]*A.f.* = *Aspergillus fumigatus*
*C.a.* = *Candida albican*
*M.c.* = *Microsporum canis*
*R.o.* = *Rhizopus oryzae*
*T.m.* = *Trychophyton mentagrophytes*
[b]Dissolved in 0.1M NaOAc pH 4.6 buffer.

EXAMPLE 10

Set forth below are some illustrative topical formulations containing a selected tetraalkyldiamide compound (weight %) of the instant invention.

| Formulation Number 1 - Solution | |
|---|---|
| β-dichloroamino-isovaleric acid (II) | 0.01-15% |
| Distilled water | qs to 100% |

Procedure: Dissolve compound (II) in enough water to make 100%. Filter the solution. Apply to the effected area.

| Formulation Number 2 - Tincture | |
|---|---|
| 4-dichloroamino-4-methylvaleric acid (III) | 0.01-25% |
| Alcohol U.S.P. | 50% |
| Water | qs to 100% |

Procedure: Dissolve compound (III) in the alcohol. Add sufficient water to make 100%. Filter and apply to affected area.

| Formulation Number 3 - Topical Aerosol | |
|---|---|
| 2-dichloroamino-2-methyl-1-propyl hemiglutarate (IV) | 0.01-10% |
| Alcohol U.S.P. | 5% |
| Isopropylmyristate | 5% |

The above solution is incorporated into a propellant system, such as, for example, conventional halogenated hydrocarbon propellant qs 100% e.g. Freon 11(trichloro-fuluromethane), Freon 12(dichlorodifluromethane), Freon 14 (carbon tetrafluoride), Freon C 318 (Octaflurocyclobutane), Freon 114 (Cryofluorane), isobutane-propane, etc.

Procedure: Dissolve Compound IV in the alcohol and isopropylmyristate. Add sufficient propellant and introduce into conventional aerosol containers either by pressure or by cold filing. Apply to affected area.

| Formulation Number 4 - Ointment | |
|---|---|
| 2-dichloroamino-2-methyl-1-propyl hemisuccinate (V) | 0.01-5% |
| Petrolatum U.S.P. | qs to 100% |

Procedure: Heat the petrolatum to 60° C. Add compound (V) and stir until thoroughly dispersed. Cool to room temperature. Apply to affected area.

What is claimed is:

1. A compound having the formula:

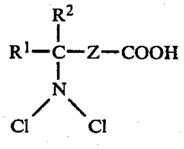

wherein $R^1$ and $R^2$ are independently
(a) lower alkyl;
(b) lower cycloalkyl;
(c) lower (cycloalkyl-alkyl);
(d) phenyl or lower alkyl-substituted phenyl;
(e) halosubstituted phenyl;
(f) lower alkoxy-substituted phenyl;
(g) phenyl (lower alkyl); or $R^1$ and $R^2$ joined together form lower alkylene; and Z is
(a) lower alkylene;
(b) $-(CH_2)_n$-phenylene-$(CH_2)_m-$ wherein n and m independently are integers from 0 to 5;

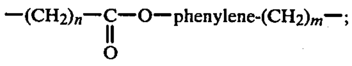 (c)

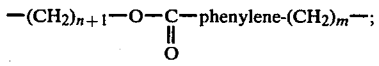 (d)

(e) $-(CH_2)_{n+1}-O-(CH_2)_m-$; wherein n is an integer from 0 to 3 and m an inter from 0-20;

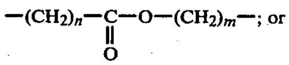 (f)

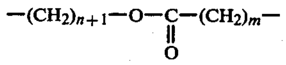 (g)

or a pharmaceutically acceptable salt thereof.

2. The compound of claim 1 wherein
$R^1$ and $R^2$ independently are lower alkyl; or
$R^1$ and $R^2$ are joined together to form lower alkylene; and
Z is
(a) lower alkylene;
(b) $-(CH_2)_{n+1}-O-(CH_2)_m-$;

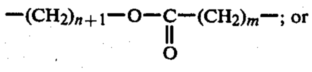 (c)

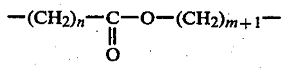 (d)

3. The compound of claim 1 wherein
$R^1$ and $R^2$ independently are $C_{1-5}$ alkyl and;
Z is
(a) $C_{1-5}$ alkylene;
(b) $-(CH_2)_{n+1}-O-(CH_2)_m-$;

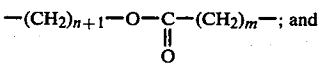 (c)

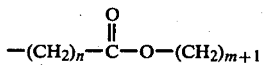 (d)

with the proviso that m is an integer from 0 to 10; and n is an integer from 0 to 3.

4. The compound of claim 1 wherein
$R^1$ and $R^2$ are methyl; and
Z is
(a) methylene or dimethylene;

(b) 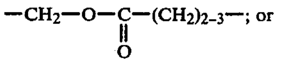

(c) 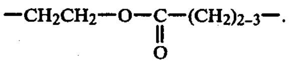

5. The compound of claim 1 which is
(a) 2-dichloroamino-isovaleric acid;
(b) 4-dichloroamino-4-methyl-valeric acid;
(c) 2-dichloroamino-2-methyl-1-propyl hemiglutarate; or
(d) 2-dichloroamino-2-methyl-1-propyl hemisuccinate or a pharmaceutically acceptable salt thereof.

6. A method of preventing and/or controlling bacterial or fungal contamination in (a) environments; (b) treatment of food items; (c) personal hygiene; and (d) veterinary hygiene comprising the spreading, spraying or application therein an efficient amount of a compound of structural formula

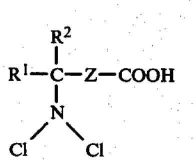

wherein $R^1$ and $R^2$ are independently (a) lower alkyl;

(b) lower cycloalkyl;

(c) lower (cycloalkyl-alkyl);

(d) phenyl or lower alkyl-substituted phenyl;

(e) halosubstituted phenyl;

(f) lower alkoxy-substituted phenyl;

(g) phenyl (lower alkyl); or $R^1$ and $R^2$ joined together form lower alkylene; and Z is (a) lower alkylene;

(b) $-(CH_2)_n$-phenylene$-(CH_2)_m-$ wherein n and m independently are integers from 0 to 5;

$$-(CH_2)_n-\underset{\substack{\| \\ O}}{C}-O-\text{phenylene-}(CH_2)_m-; \quad (c)$$

$$-(CH_2)_{n+1}-O-\underset{\substack{\| \\ O}}{C}-\text{phenylene-}(CH_2)_m-; \quad (d)$$

(e) $-(CH_2)_{n+1}-O-(CH_2)_m-$; wherein n is an integer from 0 to 3 and m an inter from 0–20;

$$-(CH_2)_n-\underset{\substack{\| \\ O}}{C}-O-(CH_2)_m-; \text{ or} \quad (f)$$

$$-(CH_2)_{n+1}-O-\underset{\substack{\| \\ O}}{C}-(CH_2)_m- \quad (g)$$

or a pharmaceutically acceptable salt thereof.

7. The method of claim 6 wherein the compound is (a) 2-dichloroamino-isovaleric acid;

(b) 4-dichloroamino-4-methyl-valeric acid;

(c) 2-dichloroamino-2-methyl-1-propyl hemiglutarate;

(d) 2-dichloroamino-2-methyl-1-propyl hemisuccinate; or a pharmaceutically acceptable salt thereof.

8. A pharmaceutical composition for preventing and/or controlling bacterial or contamination in (a) environmental sanitation; (b) treatment of food items; (c) personal hygiene and (d) veterinary hygiene comprising a pharmaceutical carrier and an effective amount of a compound of the structural formula: wherein

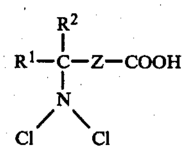

wherein $R^1$ and $R^2$ are independently (a) lower alkyl;

(b) lower cycloalkyl;

(c) lower(cycloalkyl-alkyl);

(d) phenyl or lower alkyl-substituted phenyl;

(e) halosubstituted phenyl;

(f) lower alkoxy-substituted phenyl;

(g) phenyl(lower alkyl); or $R^1$ and $R^2$ joined together form lower alkylene; and Z is (a) lower alkylene;

(b) $-(CH_2)_n-$phenylene$-(CH_2)_m-$ wherein n and m independently are integers from 0 to 5;

$$-(CH_2)_n-\underset{\substack{\| \\ O}}{C}-O-\text{phenylene-}(CH_2)_m-; \quad (c)$$

$$-(CH_2)_{n+1}-O-\underset{\substack{\| \\ O}}{C}-\text{phenylene-}(CH_2)_m-; \quad (d)$$

(e) $-(CH_2)_{n+1}-O-(CH_2)_m-$; wherein n is an integer from 0 to 3 and m an inter from 0–20;

$$-(CH_2)_n-\underset{\substack{\| \\ O}}{C}-O-(CH_2)_m-; \text{ or} \quad (f)$$

$$-(CH_2)_{n+1}-O-\underset{\substack{\| \\ O}}{C}-(CH_2)_m- \quad (g)$$

or a pharmaceutically acceptable salt thereof.

9. The pharmaceutical composition of claim 8 wherein $R^1$, $R^2$, $R^3$ and Z of the active compound are defined according to claim 2, 3, or 4.

10. The pharmaceutical composition of claim 8 wherein the compound is (a) 2-dichloroamino-isovaleric acid;

(b) 4-dichloroamino-4-methyl-valeric acid;

(c) 2-dichloroamino-2-methyl-1-propyl hemiglutarate;

(d) 2-dichloroamino-2-methyl-1-propyl hemisuccinate;

or a pharmaceutically acceptable salt thereof.

* * * * *